United States Patent
Petroskie

(10) Patent No.: US 9,395,268 B2
(45) Date of Patent: Jul. 19, 2016

(54) METHOD AND SYSTEM TO TOLERANCE TEST A COMPONENT

(71) Applicant: General Electric Company, Schenectady, NY (US)

(72) Inventor: Robert Michael Petroskie, Roebuck, SC (US)

(73) Assignee: General Electric Company, Schenectady, NY (US)

( * ) Notice: Subject to any disclaimer, the term of this patent is extended or adjusted under 35 U.S.C. 154(b) by 513 days.

(21) Appl. No.: 13/934,420

(22) Filed: Jul. 3, 2013

(65) Prior Publication Data

US 2015/0012236 A1 Jan. 8, 2015

(51) Int. Cl.
| | |
|---|---|
| *G01M 13/00* | (2006.01) |
| *G01M 13/02* | (2006.01) |
| *G01B 11/25* | (2006.01) |
| *G01N 21/95* | (2006.01) |
| *G06T 7/00* | (2006.01) |
| *G06F 11/263* | (2006.01) |

(52) U.S. Cl.
CPC ............ *G01M 13/025* (2013.01); *G01M 13/00* (2013.01); *G01B 11/25* (2013.01); *G01B 11/2504* (2013.01); *G01N 21/9515* (2013.01); *G06F 11/263* (2013.01); *G06T 7/0057* (2013.01)

(58) Field of Classification Search
CPC .... G01M 13/025; G01M 13/00; G01B 11/25; G01B 11/2504; G06T 7/0057; G01N 21/9515; G06F 11/263
USPC ......... 702/39, 85, 113, 119, 152, 182; 73/588
See application file for complete search history.

(56) References Cited

U.S. PATENT DOCUMENTS

| | | | | |
|---|---|---|---|---|
| 4,057,714 | A | | 11/1977 | Fork et al. |
| 4,156,188 | A | * | 5/1979 | Kreissl .................... G01R 33/12 324/545 |
| 5,105,365 | A | * | 4/1992 | McDaniel ............. G06F 17/243 702/24 |
| 5,837,879 | A | * | 11/1998 | Zick .......................... H02P 1/12 73/1.37 |
| 6,041,287 | A | | 3/2000 | Dister et al. |
| 6,059,545 | A | | 5/2000 | Straub et al. |
| 6,134,674 | A | * | 10/2000 | Akasheh ............... G06F 11/263 714/33 |
| 6,290,556 | B1 | | 9/2001 | Howland et al. |
| 6,324,486 | B1 | * | 11/2001 | Crook ................ G01R 31/2834 324/537 |
| 6,671,573 | B2 | | 12/2003 | Nigazawa et al. |
| 6,915,695 | B2 | | 7/2005 | Weiss et al. |
| 7,206,717 | B2 | * | 4/2007 | Hardy ..................... G01B 11/25 702/152 |
| 7,483,125 | B2 | * | 1/2009 | Collings ............ H04B 10/2513 356/73.1 |
| 7,685,731 | B1 | | 3/2010 | Petroskie et al. |

(Continued)

*Primary Examiner* — Carol S Tsai
(74) *Attorney, Agent, or Firm* — Ernest G. Cusick; Hoffman Warnick LLC

(57) ABSTRACT

A method and system of tolerance testing a component using data measurements from a single test setup within a test apparatus are described. The method includes receiving the data measurements obtained with the single test setup. The method also includes separating, at the processor, the data measurements from a relative positioning of an element of the test apparatus and performing, at the processor, a virtual setup of the component to obtain additional data measurements related to one or more parts of the component. The method additionally includes determining, at the processor, whether a parameter associated with the one or more parts meets a specified tolerance based on the additional data measurements obtained from the virtual setup.

12 Claims, 7 Drawing Sheets

(56) References Cited

U.S. PATENT DOCUMENTS

| | | |
|---|---|---|
| 7,877,891 B2 | 2/2011 | Petroskie et al. |
| 8,169,515 B2 * | 5/2012 | Wilkinson ............ H04N 5/3595 348/234 |
| 2006/0167643 A1 * | 7/2006 | Casto ................... G01R 35/005 702/85 |
| 2006/0290918 A1 * | 12/2006 | Collings ............ H04B 10/2513 356/73.1 |
| 2010/0114515 A1 * | 5/2010 | Casto ...................... G06F 11/24 702/85 |
| 2011/0172946 A1 * | 7/2011 | Bazemore ................. G01S 7/40 702/119 |
| 2012/0150472 A1 * | 6/2012 | Trager ................ G01M 99/008 702/113 |
| 2013/0046480 A1 * | 2/2013 | Manri .................. G01N 21/272 702/19 |
| 2013/0339930 A1 * | 12/2013 | Xu ...................... G06F 11/3684 717/125 |

\* cited by examiner

METHOD AND SYSTEM TO TOLERANCE TEST A COMPONENT

BACKGROUND OF THE INVENTION

The subject matter disclosed herein relates to tolerance testing components.

The various components of a system, such as a rotor stub shaft, for example, often must be individually tolerance tested prior to their incorporation into the system. Specifically, various elements of the component may be checked individually for form control (e.g., circularity for a diameter, flatness for a planar surface) and also to ensure that the relative location of elements (e.g., eccentricity for a diameter) is within required tolerances. In many cases this tolerance testing requires multiple set up operations of a probing tool. For example, when a shaft is tested, different sets of measurements (circumferential and axial) are taken to determine parameters such as circularity and eccentricity each time the shaft is set up for probing to determine relative variations of different elements of the shaft. Each set of these measurements is taken by setting the part in a lathe and rotating or moving the shaft while measuring an offset (run out) of one or more probes from their initial positions. This method of measurement is prone to false positive or false negative results based on how the lathe is positioned within the shaft during the measurements. That is, for example, if the shaft is not centered within the lathe, the probe may experience offsets due to the wobble created by rotation on the un-centered shaft rather than due to variations in the form and location of the shaft. In addition, the specific verification of relative location of different parts (elements) of the shaft requires a different setup (positioning of the lathe) for each such verification.

BRIEF DESCRIPTION OF THE INVENTION

According to one aspect of the invention, a method of tolerance testing a component using data measurements from a single test setup within a test apparatus includes receiving, at a processor, the data measurements obtained with the single test setup; separating, at the processor, the data measurements from a relative positioning of an element of the test apparatus; performing, at the processor, a virtual setup of the component to obtain additional data measurements related to one or more parts of the component; and determining, at the processor, whether a parameter associated with the one or more parts meets a specified tolerance based on the additional data measurements obtained from the virtual setup.

According to another aspect of the invention, a system to tolerance test a component using data measurements from a single test setup within a test apparatus includes an input interface configured to receive the data measurements from the single test setup; and a processor configured to separate the data measurements from a relative positioning of an element of the test apparatus, perform a virtual setup of the component to obtain additional data measurements related to one or more parts of the component, and determine whether a parameter associated with the one or more parts meets a specified tolerance based on the additional data measurements obtained from the virtual setup.

According to yet another aspect of the invention, a non-transitory computer-readable medium stores instructions which, when processed by a processor, cause the processor to implement a method of tolerance testing a component using data measurements from a single test setup within a test apparatus. The method includes receiving, at a processor, the data measurements obtained with the single test setup; separating, at the processor, the data measurements from a relative positioning of an element of the test apparatus; performing, at the processor, a virtual setup of the component to obtain additional data measurements related to one or more parts of the component; and determining, at the processor, whether a parameter associated with the part meets a specified tolerance based on the additional data measurements obtained from the virtual setup.

These and other advantages and features will become more apparent from the following description taken in conjunction with the drawings.

BRIEF DESCRIPTION OF DRAWINGS

The subject matter, which is regarded as the invention, is particularly pointed out and distinctly claimed in the claims at the conclusion of the specification.

The foregoing and other features, and advantages of the invention are apparent from the following detailed description taken in conjunction with the accompanying drawings in which.

The detailed description explains embodiments of the invention, together with advantages and features, by way of example with reference to the drawings.

DETAILED DESCRIPTION OF THE INVENTION

As noted above, the currently used methodology to verify that a component meets specified tolerances is prone to error and requires re-setup and re-run for each verification of a different set of elements of the component. Embodiments of the system and method described herein relate to obtaining measurements using a single setup and post-processing the measurements for more accurate tolerance assessments without the need for additional measurements using different test setup configurations. As detailed below, by obtaining measurements with a part reference set by the lathe axis, analysis may also be performed for a part reference set by a part axis defined by two part diametric sets, and a part set normal to a selected axial data (face) set and centered on a selected diametric data (center) set. While a shaft is used as an exemplary component in the description of the embodiments below, alternate embodiments of the system and methods described may apply, as well, to other components being tolerance tested.

Figure 1:
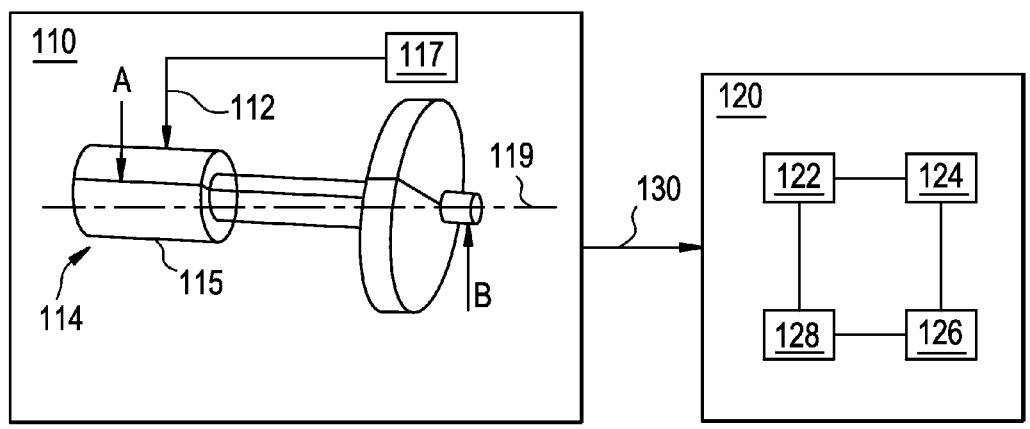
FIG. 1 depicts a system to tolerance test a component according to an embodiment of the invention.

FIG. 1 depicts a system to tolerance test a component 114 according to an embodiment of the invention. The exemplary component 114 shown in FIG. 1 is a shaft 115. The exemplary parameters whose tolerances are of interest with reference to the shaft 115 are circularity (form control for the diameter) and eccentricity (location control for the diameter). As shown in FIG. 1, the component 114 (shaft 115) is set up within a test apparatus 110 that may include one or more probe devices 112 and a controller 117 that rotates the shaft (component 115) about a lathe 119 or moves the probe 112 along the axial length of the shaft 115 and records the displacement of the probe 112 (the run out). For example, when the shaft 115 is rotated about the lathe 119, any displacement of the probe 112 (up or down from its original position) may indicate non-uniform circularity of the shaft 115 at the axial position at which the probe 112 is shown in FIG. 1. The arrangement in FIG. 1 illustrates one of the issues resulting from relying solely on measurements taken by the controller 117. As shown in FIG. 1, the lathe 119 is not perfectly centered within the shaft 115. This creates a wobble effect when the shaft 115 is rotated about the lathe 119, and a false reading of non-circularity is likely even if the shaft 115 were perfectly circular at the axial position shown for the probe 112. This wobble effect may be addressed through the setup in the following way. When probes are disposed at two elements (A and B) with the lathe 119 centered within the shaft 115 at least at axial positions of the two elements (A and B), then a wobble is identifiable based on both probes being displaced at the same radial positions. That is, as the shaft 115 is rotated, the probes (at A and B) would not be displaced at all if circularity were perfect at A and B and the lathe 119 were perfectly centered within the shaft 115 at A and B. If circularity were perfect at A and B but a wobble resulted from the lathe 119 position, then both probes (at A and B) would be displaced at the same time during rotation. If circularity were not perfect at A or B, then the probes would likely be displaced independently of each other. Embodiments of the invention facilitate virtual setup of the component 114 to verify circularity (a form control parameter) and eccentricity (a location control parameter) within specified tolerances without the burden and uncertainty associated with the physical test apparatus 110.

According to embodiments of the present invention, the measurement data 130 from the test apparatus 110 is provided to an analyzer 120. The analyzer 120 includes one or more processors 122, one or more memory devices 124, an input interface 126, and an output interface 128. The analyzer 120 receives the measurement data 130 from the test apparatus 110 through the input interface 126 and provides an analysis of whether parameters at various elements (e.g., circularity at A and B) of the component 114 meet required tolerances. The measurement data 130 is provided for a single setup of the test apparatus 110. For example, the setup may be as shown in FIG. 1 with the lathe 119 not centered within the shaft 115. Because the analyzer 120 separates the parameter measurement (e.g., circularity, eccentricity) from the location (relative to the lathe 119) in the measurement data 130, as discussed further below, the analyzer 120 uses modeling to virtually set up the component 114, as needed, to compare selected elements for a determination of how closely they meet specified tolerances. The analyzer 120 uses models and instructions stored in the memory device 124 to process the measurement data 130 with the processor 122 and output the result via the output interface 128. The output may be, for example, parameter values based on the virtual setup or a determination of whether the parameter meets the specified tolerance.

Figure 2:
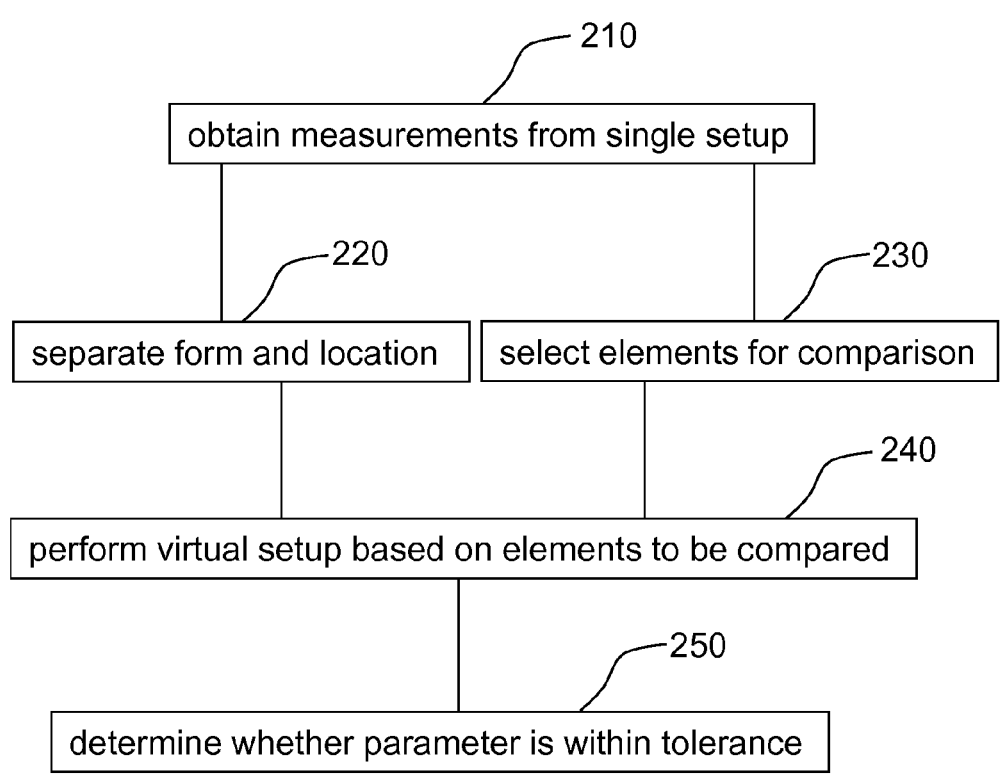
FIG. 2 is a flow diagram of a method of tolerance testing a component according to embodiments of the invention.

FIG. 2 is a flow diagram of a method of tolerance testing a component 114 according to embodiments of the invention. At block 210, the method includes obtaining measurements (measurement data 130) from a single setup of the component 114 in the test apparatus 110 at the analyzer 120. Separating the form control parameters (e.g., circularity and flatness measurement data 130) and location control parameters (e.g., eccentricity, which is relative to the lathe 119 position for the particular test apparatus 110 setup in FIG. 1) at block 220 is detailed further below. Selecting elements for comparison at block 230 may be based on a pre-programmed sequence or on user input. At block 240, performing virtual setup based on the elements to be compared (according to block 230) involves the modeling discussed further below. Determining whether a parameter (e.g., circularity, flatness, eccentricity) is within the specified tolerance at block 250 is based on the virtual setup (at block 240). The processes detailed herein have the technical effect of tolerance testing elements of a component based on obtaining measurements data 130 from a single setup of the physical test apparatus 110.

Figure 3:
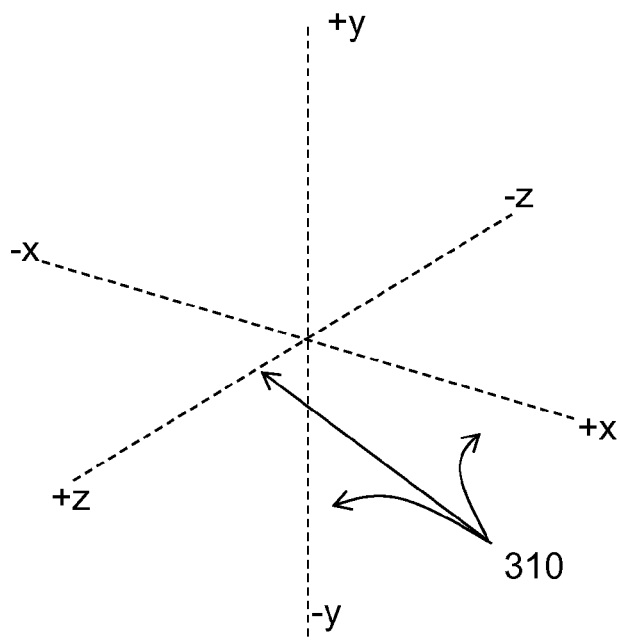
FIG. 3 depicts the test apparatus coordinate system reference defined as part of the method described with reference to FIG. 2.
Figure 4:
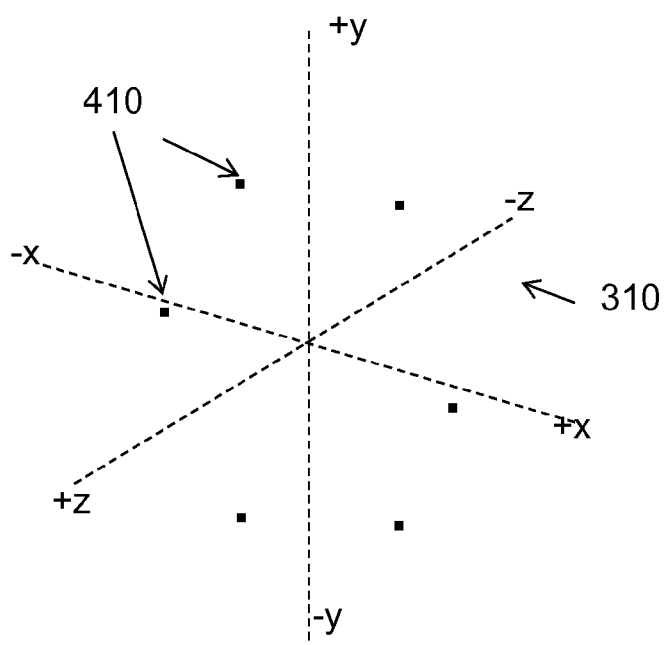
FIG. 4 depicts the measurement data for one probe location plotted on the three-dimensional coordinate system shown in FIG. 3.
Figure 5:
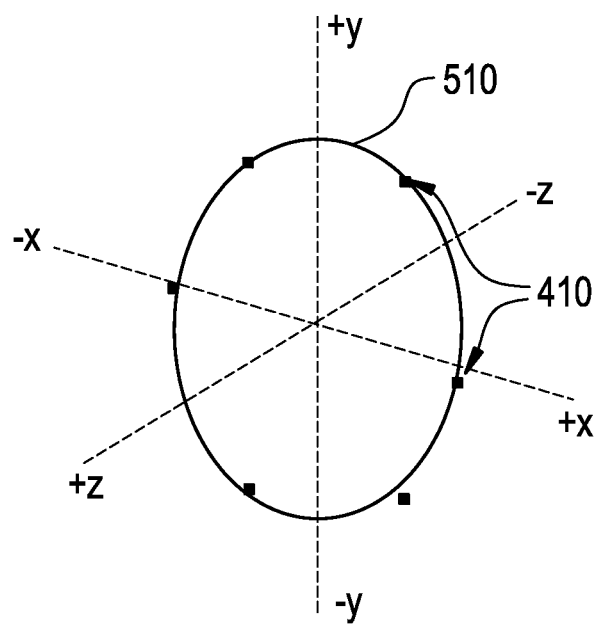
FIG. 5 depicts a best-fit circle drawn for the measurements data plotted in FIG. 4.
Figure 6:
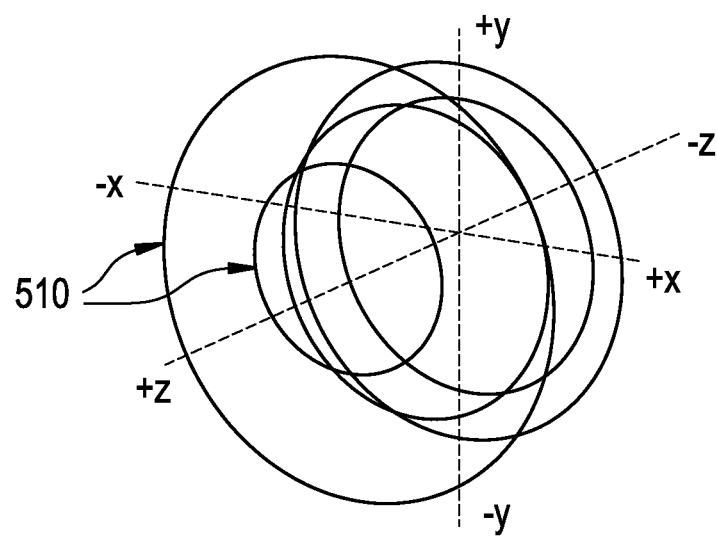
FIG. 6 additionally depicts best-fit circles for the other probe positions resulting in the measurement data.
Figure 7:
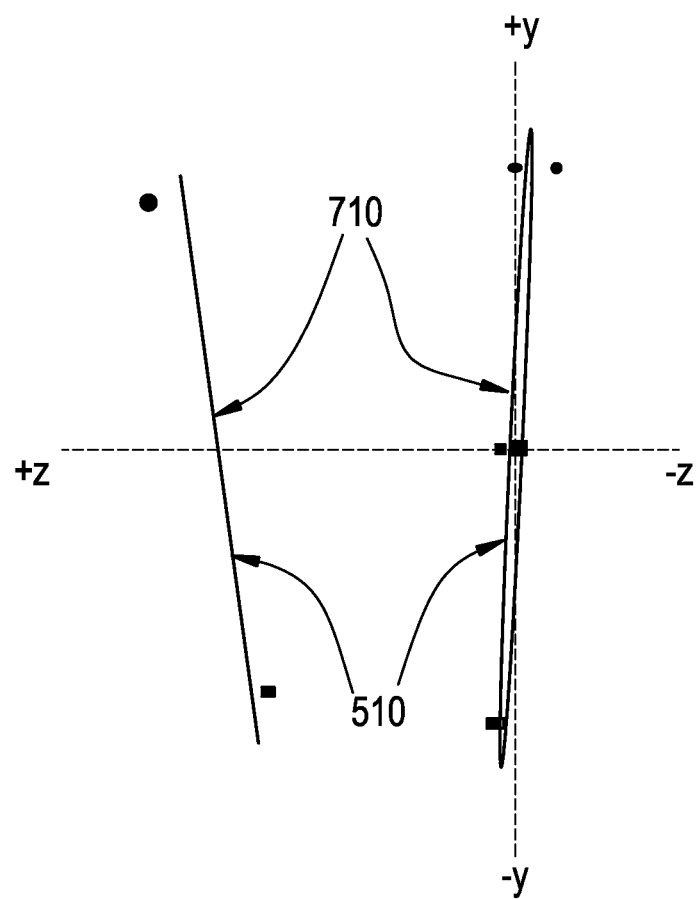
FIG. 7 depicts best-fit planes viewed as the best-fit circles from the x-axis.

FIGS. 3-11 detail processes involved in separating the form control parameters and location control parameters in measurement data 130 and performing virtual setup. These processes apply known techniques to the measurement data 130 to achieve the virtual setup, as detailed below. FIG. 3 depicts the test apparatus 110 coordinate system reference defined as part of the method described with reference to FIG. 2. A three-dimensional coordinate system 310 is defined based on the test apparatus 110 that was used to obtain the measurement data 130. FIG. 4 depicts the set of points 410 in the measurement data 130 for one feature (e.g., element of the shaft such as a radial probe position or face) plotted on the three-dimensional coordinate system 310 shown in FIG. 3. FIG. 5 depicts a best-fit circle 510 drawn for the measurements data 130 plotted in FIG. 4. The best-fit circle 510 may be obtained using known curve fitting techniques. The radial data sets shown in FIG. 5 include both form control and location control parameters. FIG. 6 additionally depicts best-fit circles 510 for sets of points in the measurement data 130 for the other features. FIG. 7 depicts best-fit planes 710 viewed as the best-fit circles 510 from the x-axis. As with the best-fit circles 510, the process of determining the best-fit plane 710 is repeated for each set of points in the measurement data 130 associated with a feature. Like the best-fit circles 510 shown in FIG. 5, the axial data sets shown in FIG. 7 include both form control and location control parameters. The best-fit circles 510 and best-fit planes 710 facilitate the separation of the forms of each of the elements (e.g., circularity, flatness) from the location (e.g., eccentricity, parallelism) relative to the lathe 119 (FIG. 1) and the other elements.

Figure 8:
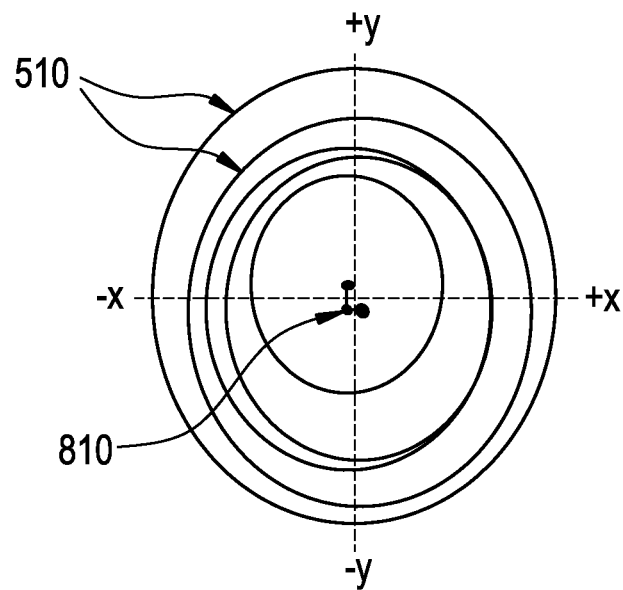
FIG. 8 depicts the best fit circles from the z-axis.
Figure 9:
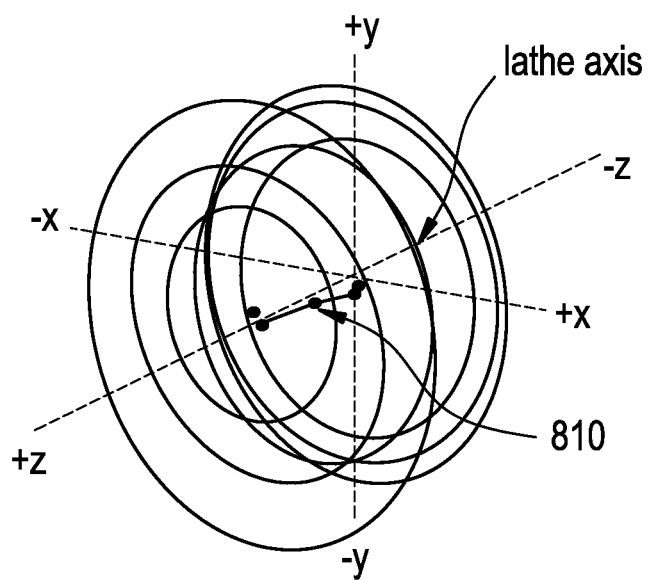
FIG. 9 depicts the shaft axis in the three-dimensional coordinate system.

FIG. 8 depicts the best fit circles 510 from the z-axis. The centers of each of the best-fit circles 510 determine the shaft 115 axis 810. To be clear, regardless of the setup of the shaft 115 in the test apparatus 110 (relative to the lathe 119) to obtain the measurement data 130, the process described above may be used to determine the shaft 115 axis 810. This shaft axis 810 is shown in the three-dimensional coordinate system 310 in FIG. 9. The lathe 119 axis lines up with the z-axis of the three-dimensional coordinate system 310. Once the shaft 115 axis 810 is determined, the points of the measurement data 130 may be moved to perform virtual set ups in the following way. Because the shaft 115 axis 810 is fixed (parts of the shaft do not move relative to each other), the points of the measured data 130 are moved altogether. A virtual setup means that the points of the measured data 130 are moved (together) so that the shaft 115 axis 810 points corresponding with features of interest are on the z-axis of the three dimensional coordinate system 310. This is shown with reference to FIGS. 10 and 11.

Figure 10:
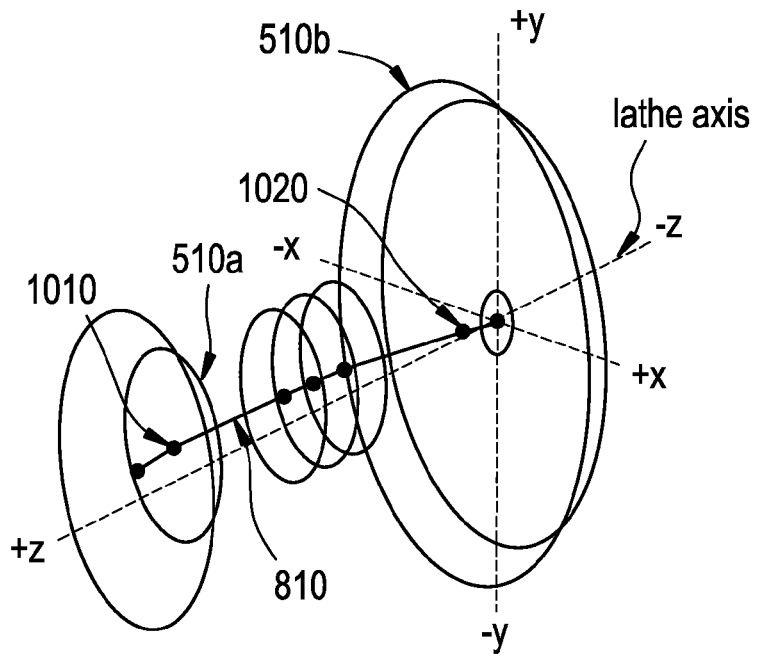
FIG. 10 depicts points from the measurement data in the form of best-fit circles and the shaft axis determined via the process described with reference to FIGS. 3-9.
Figure 11:
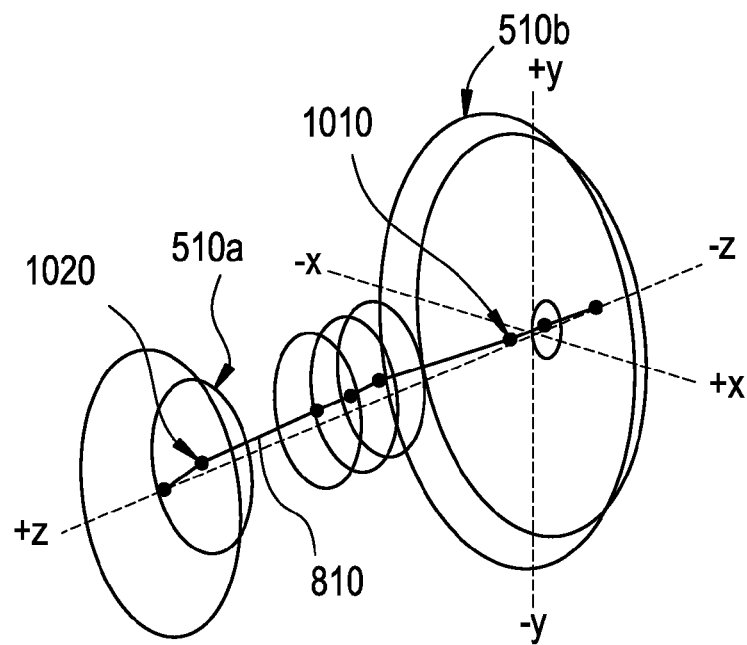
FIG. 11 depicts the points from the measurement data shifted within the three-dimensional coordinate system.

FIG. 10 depicts points from the measurement data 130 in the form of best-fit circles 510 and the shaft 115 axis 810 determined via the process described above. As noted above, the lathe 119 axis is along the z-axis. The features (points among the measurement data 130) of interest correspond with the best-fit circles 510a and 510b having centers 1010 and 1020, respectively. FIG. 11 shows the points from the measurement data 130 (shown as best-fit circles 510) shifted within the three-dimensional coordinate system 310. The shaft 115 axis 810 is maintained while the centers 1010 and 1020 corresponding to the features of interest are moved onto the z-axis. The points corresponding to best-fit circles 510a and 510b may be used to determine compliance with specified tolerances based on the shift (virtual setup) shown in FIG. 11. For example, circularity of best-fit circle 510a may be determined based on the relative distance of the points used to make up the best-fit circle 510a from the z-axis. Eccentricity may be determined by comparing the distance of the points corresponding with best-fit circle 510a from the center 1010 with the distance of the respective points corresponding with best-fit circle 510b from the center 1020. In this way, the virtual setup achieved by shifting the shaft 115 axis 810 facilitates tolerance testing without multiple runs of the test apparatus 110.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A system to tolerance test a component using data measurements from a single test setup within a test apparatus, the system comprising:
   an input interface configured to receive the data measurements from the single test setup; and
   a processor configured to separate the data measurements from a relative positioning of an element of the test apparatus, perform a virtual setup of the component to obtain additional data measurements related to one or more parts of the component, and determine whether a parameter associated with the one or more parts meets a specified tolerance based on the additional data measurements obtained from the virtual setup.

2. The system according to claim 1, wherein the component is a shaft and the element of the test apparatus is a lathe.

3. The system according to claim 1, wherein the parameter is circularity.

4. The system according to claim 1, wherein the additional data measurements are related to two or more parts of the component, and the parameter is eccentricity.

5. The system according to claim 1 wherein the processor separates the data measurements from the relative positioning of the element based on plotting the data measurements on a three-dimensional coordinate system referenced to the element of the test apparatus.

6. The system according to claim 5, wherein the processor determines an axis through the component based on the plotting the data measurements.

7. The system according to claim 1, wherein the processor performs the virtual setup relative to the one or more parts.

8. A method using a non-transitory computer-readable medium storing instructions which, when processed by a processor, cause the processor to implement tolerance testing of a component using data measurements from a single test setup within a test apparatus, the method comprising:
   receiving the data measurements obtained with the single test setup;
   separating the data measurements from a relative positioning of an element of the test apparatus;
   performing a virtual setup of the component to obtain additional data measurements related to one or more parts of the component; and
   determining whether a parameter associated with the one or more parts meets a specified tolerance based on the additional data measurements obtained from the virtual setup.

9. The method according to claim 8, further comprising plotting the data measurements on a three-dimensional coordinate system referenced to the element of the test apparatus.

10. The method according to claim 9, further comprising determining an axis through the component based on the plotting the data measurements.

11. The method according to claim 8, wherein the parameter is circularity.

12. The method according to claim 8, wherein the additional data measurements are related to two or more parts and the parameter is eccentricity.

* * * * *